United States Patent [19]

Kirsch et al.

[11] Patent Number: 4,719,109
[45] Date of Patent: Jan. 12, 1988

[54] EM5596—AN ANTIBIOTIC

[75] Inventors: Donald R. Kirsch, Princeton; Edward Meyers, East Brunswick; Joseph E. Biskupiak, Plainsboro, all of N.J.

[73] Assignee: E. R. Squibb & Sons, Inc., Lawrenceville, N.J.

[21] Appl. No.: 30,536

[22] Filed: Mar. 27, 1987

[51] Int. Cl.$^4$ .......................... H61C 35/70; C12P 1/06
[52] U.S. Cl. ...................................... 424/117; 435/171
[58] Field of Search ......................... 424/117; 435/171

[56] References Cited

U.S. PATENT DOCUMENTS 3,689,639  9/1972  Bergy et al. ..................... 424/117

FOREIGN PATENT DOCUMENTS 0112233  6/1984  European Pat. Off. ........... 424/117

Primary Examiner—Jerome D. Goldberg
Attorney, Agent, or Firm—Lawrence S. Levinson; Donald J. Barrack

[57] ABSTRACT

A novel antibiotic substance EM5596 is prepared by cultivation of a strain of the microorganism *Micrococcus luteus* A.T.C.C. No. 53598.

3 Claims, 4 Drawing Figures

EM5596—AN ANTIBIOTIC

Cultivation of a strain of the microorganism *Micrococcus luteus* that has been deposited in the American Type Culture Collection as A.T.C.C. No. 53598 yields the novel antibiotic substance EM5596 having activity against gram positive bacteria. EM5596 can be used as a growth promoter and to enhance the feed efficiency in chickens and swine.

DETAILED DESCRIPTION OF THE INVENTION

The Microorganism

Figure 1:
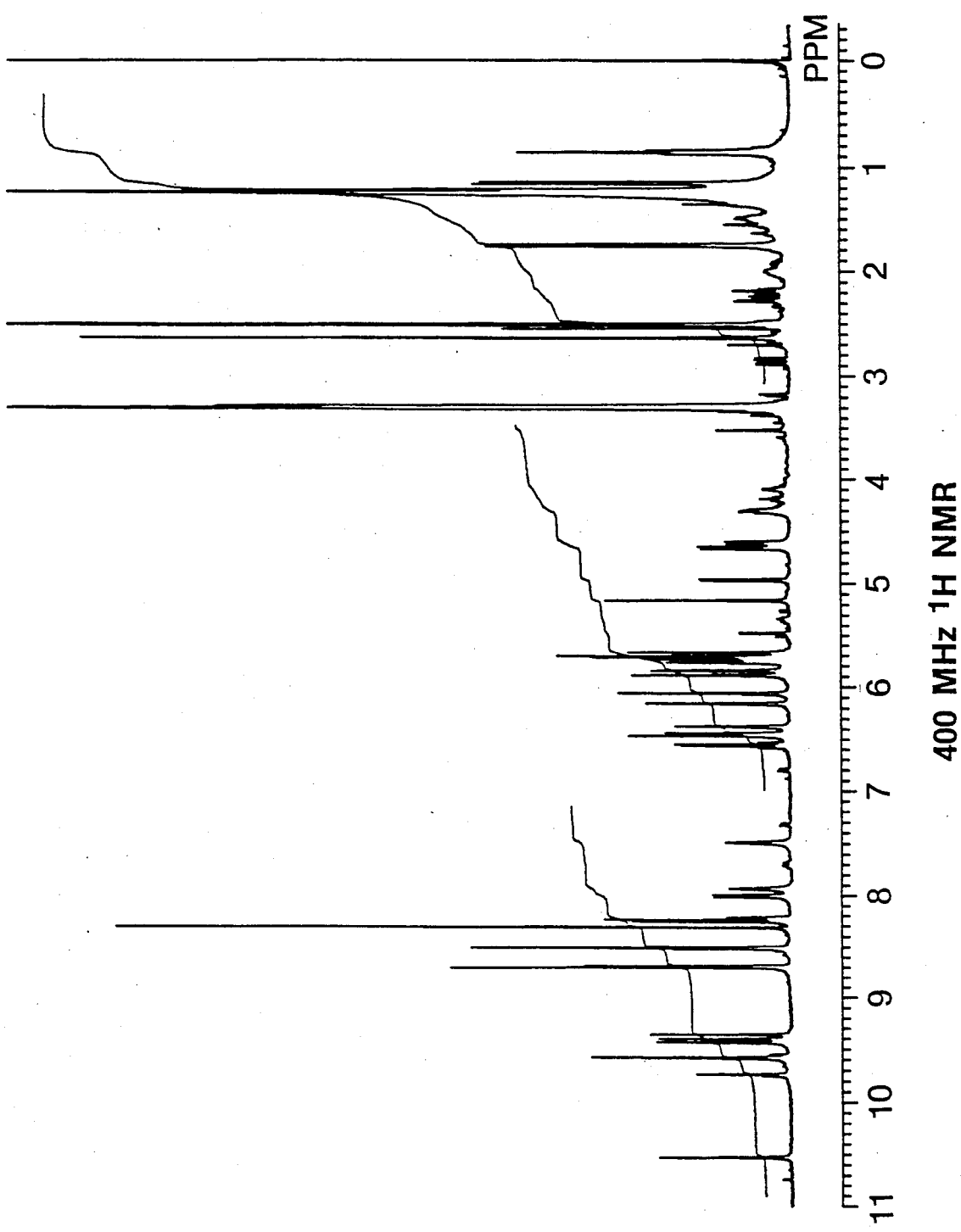
FIG. 1 shows the 400 MHz $^1$H NMR spectrum of EM5596 in deuterated dimethylsulfoxide.

The microorganism used for the production of EM5596 is a strain of *Micrococcus luteus* isolated from the soil. A subculture of the organism can be obtained from the permanent collection of the American Type Culture Collection, Rockville, Md. Its accession number in the repository is A.T.C.C. No. 53598. In addition to the specific microorganism described and characterized herein, it should be understood that mutants of the microorganism (e.g., mutants produced through the use of x-rays, ultraviolet radiation, mutagens, etc.) can also be cultivated to produce EM5596.

*Micrococcus luteus* A.T.C.C. No. 53598, can be isolated from a soil sample in which it is present (in this instance obtained in Voorhees State Park, Highbridge, N.J.) by first suspending the sample in sterile diluent (e.g., buffered saline containing 0.01% gelatin) and shaking. A dilution of this suspension is plated onto a nutrient medium that has been supplemented with cycloheximide. The composition of this medium is:

|  | Grams |
| --- | --- |
| Yeast extract | 0.4 |
| Mannitol | 10.0 |
| $K_2HPO_4$ | 0.1 |
| NaCl | 0.1 |
| $MgSO_4.7H_2O$ | 0.2 |
| Agar | 18.0 |
| Congo red | 10.0 ml of a 25% aqueous solution |
| Soil extract solution* | 190 ml |
| Tap water | 800 ml |
| Cycloheximide** | 1% aqueous solution |

*The soil extract filtrate is made by boiling a suspension of soil in water (1:2, w/v) for 1 hour and filtering the cooled extract.
**Filter sterilized and added to the medium that has already been adjusted to pH about 6.8 and sterilized by autoclaving at 121° C. for 30 minutes.

After four days incubation at about 25° C., the colonies of *Micrococcus luteus* A.T.C.C. No. 53598 are isolated from the plated soil. The isolated colonies are picked off onto an agar medium composed of:

|  | Grams |
| --- | --- |
| Yeast extract | 5.0 |
| Glucose | 5.0 |
| $MgSO_4.7H_2O$ | 0.1 |
| $FeSO_4.7H_2O$ | 0.1 |
| Agar | 17.5 |
| Soil extract filtrate* | 200 ml |
| Tap water | 800 ml |

*The soil extract is prepared as described above.

The medium is sterilized by autoclaving at 121° C. for 15 minutes.

*Micrococcus luteus* A.T.C.C. No. 53598 is a gram positive coccus arranged in tetrads and irregular clumps of tetrads. Colonies are smooth with a dull surface and are pigmented yellow. The cells are not motile. The mole % G+C of the DNA is 67. The organism does not produce acid from glucose either aerobically or anaerobically. These data establish the genus of the organism as Micrococcus The organism is positive in the oxidase, catalase and gelatin hydrolysis assays but is negative in tests for nitrate reduction, arginine dihydrolase, esculin hydrolysis, acetoin production and β-galactosidase. No growth occurs on Simmon's Citrate Agar or on a synthetic medium with ammonium dihydrogen phosphate as the sole source of nitrogen. It is sensitive to the lytic action of lysozyme.

These characteristics serve to identify the culture as *Micrococcus luteus* in accordance with the description of this organism (Schleifer, K. H.; W. E. Kloos, and M. Kocur, 1981. The Genus Micrococcus, p. 1539 to 1547. In M. P. Starr, H. Stolp, H. G. Truper, A. Balows and H. G. Schleigel (Eds.). The Procaryotes. Vol. II. Springer-Verlag, New York).

The Antibiotic

The antibiotic EM5596 can be produced by cultivating *Micrococcus luteus* A.T.C.C. No. 53598 at, or about, room temperature (25° C.) under submerged aerobic conditions in an aqueous nutrient medium containing an assimilable source of carbon and an assimilable source of nitrogen. The fermentation is carried out until substantial antibiotic activity is imparted to the medium, usually about 36 to 72 hours, preferably about 48 hours. The fermentation, as well as subsequent isolation steps, can be monitored by means of a conventional paper disc-agar diffusion assay with *Staphylococcus aureus* as the assay organism. EM5596 can be isolated and purified by art-recognized techniques from both the broth supernate and the cell mass after the centrifugation of the fermentation broth.

To obtain the antibiotic from the cell mass, a methanolic extract of the cell mass is made and concentrated in vacuo to an oily residue that is then partitioned between dichloromethane and a saturated sodium chloride solution. The organic layer is chromatographed on silica gel employing a stepwise gradient of methanol in chloroform. Active fractions are pooled and purified further by reversed phase high pressure liquid chromatography on $C_{18}$ silica gel, with a 35% solution of tetrahydrofuran in water to yield pure EM5596.

EM5596 can be recovered from the broth supernate by extraction into n-butanol followed by concentration of the organic layer in vacuo and subsequent partition of the concentrate between dichloromethane and a brine solution. Further purification is effected by chromatography on silica gel with a stepwise gradient of methanol in chloroform followed by reversed phase high pressure liquid chromatography to provide pure EM5596.

The following example further illustrates this invention.

EXAMPLE 1

Preparation of EM5596

Yeast extract, glucose, soil extract, salts, agar slants were seeded with *Micrococcus luteus* A.T.C.C. No. 53598 and incubated overnight at 28° C. The subsequent growth was used to inoculate 100 ml portions of an aqueous medium contained in 500 ml Erlenmeyer flasks. The composition of the germination medium was:

|  | Grams |
|---|---|
| Oatmeal | 20 |
| Tomato paste | 20 |
| Tap water | to 1000 ml |

The medium, adjusted to pH 7.0, was sterilized at 121° C. for 15 minutes prior to use.

The inoculated germination flasks were incubated at 25° C. on a rotary shaker for about 24 hours. The shaker operated at a speed of 300 rpm with a 2 inch stroke.

A 1% transfer was made from the germination flasks to fresh flasks; 100 ml portions of the same medium contained in each of one hundred 500 ml Erlenmeyer flasks. The inoculated flasks were incubated to 25° C. for about 48 hours on a rotary shaker operating at 300 rpm with a 2 inch stroke.

At harvest, the contents of the flasks were pooled and the pooled broth was centrifuged, yielding approximately 9.8 liters of supernate and about 700 grams of solids. The solids were then suspended in 5 liters of methanol and the suspension stirred for two hours at room temperature. The liquid phase, separated from the solids by centrifugation, was concentrated at $\leq 45°$ C. in vacuo to yield approximately 50 ml of a yellow, oily residue. The residue was partitioned between 250 ml of a saturated sodium chloride solution and three 250 ml portions of dichloromethane. The organic extracts were pooled and concentrated in vacuo to give 2 grams of an orange oil.

The broth supernate, freed of suspended solids by centrifugation, was extracted with two 5 liter portions of n-butanol. The butanolic extracts were combined and concentrated in vacuo to an oily residue. The residue was partitioned between 250 ml of a saturated solution of sodium chloride and three 250 ml portions of dichloromethane. The pooled organic layers were concentrated in vacuo to give 4.6 grams of a brown oil.

About 2.0 g of the orange oil, obtained by processing the bacterial pellet as described above, was charged onto a Whatman LPS-1 silica gel column, 2.5×40 cm, packed in chloroform. The column was eluted with 500 ml portions of chloroform 1% methanol in chloroform, 5% methanol in chloroform and 10% methanol in chloroform. The flow rate was about 40 ml per minute and 250 ml fractions were collected. Each fraction was tested for bioactivity by paper disc-agar diffusion assay with *S. aureus* FDA 209P as the assay organism. The activity was found to elute in the 5% methanol/chloform eluate. The active fractions were combined and concentrated in vacuo to give 51.7 mg of crude EM5596 as a yellowish, amorphous solid. The solid was dissolved in 5 ml of a tetrahydrofuran:water 1:1, v/v mixture and 0.5 ml was then injected onto a 0.94×50 cm column of $C_{18}$-bonded silica gel (Whatman M9-50 Partisil ODS-3). Elution was accomplished with an isocratic solvent consisting of tetrahydrofuran:water, 35:65 v/v, at a flow rate of 4 ml per minute. EM5596 eluted broadly with a retention time between 45 to 90 minutes. This chromatography step was repeated until the entire sample had been run. Active fractions were pooled and concentrated in vacuo to give 22.1 mg of pure EM5596 as a colorless, amorphous solid.

EM5596 has the following characteristics: mass spectrum (FAB in a dithiothreitol, dithioerythritol, dimethylsulfoxide and glycerol matrix), highest observed peak m/z 1132: UV max (acetonitrile) 240 nm ($\epsilon 81{,}000$); IR (KBr) 3356 (br), 2954, 2924, 2853, 1662, 1636, 1504 cm$^{-1}$; $^1$H NMR (DMSO-d$_6$) $\delta$1.15 (3H, d, J=6.3 Hz), 1.21 (3H, s), 1.23 (3H, s), 1.24 (3H, s), 1.75 (3H, d, J=7.3 Hz), 2.54 (3H, s), 2.63 (3H, s), 4.30 (1H, m), 4.60 (1H, m), 4.63 (1H, m), 4.95 (1H, d, J=5.5 Hz), 5.15 (1H, s), 5.66–5.88 (7H), 5.74 (1H, s), 6.05–6.46 (5H), 6.55 (1H, q, J=7.7 Hz), 7.92 (1H, br s), 7.99 (1H, br d, J=8.8 Hz), 8.21 and 8.51 (2H, AB quartet, J=8.0 Hz), 8.50 (1H, s), 8.50 (1H, d, J=7.7 Hz), 8.68 (1H, s), 8.70 (1H, s), 9.35 (1H, s), 9.40 (1H, s), 9.43 (1H, s), 9.58 (2H, s), 9.73 (1H, s), 10.53 ppm (1H, s); elemental analysis 56.87% C; 6.56% H; 11.14% N; 3.3% S; TLC on Merck silica gel with chloroform-methanol 9:1 v/v, R$_f$0.23. These characteristics distinguish EM5596 from all other antibiotics, including the related compound, berninamycin A.

Biological Activity

The following methodology was used to determine the minimum inhibitory concentration (hereinafter referred to as "MIC") of the compound of this invention. The test organisms were grown in 20 ml of Antibiotic Assay Broth (Difco) by inoculating the broth (in tubes) with a loopful of the organism from a BHI (Difco) agar slant. The inoculated tubes were incubated at 37° C. for 18 to 24 hours. These cultures are assumed to contain $10^9$ colony forming units (CFU) per ml. The cultures were diluted 1:100 to give a final inoculum level of $10^7$ CFU per ml; dilutions were made with Yeast Beef Broth (Difco). EM5596 was dissolved in an appropriate diluent at a concentration of 1,000 $\mu$g/ml. Two-fold dilutions were made in yeast Beef Broth (Difco), resulting in a range from 1000 $\mu$g/ml to 0.5 $\mu$g/ml. A 1.5 ml portion of each dilution was placed into individual petri dishes to which 13.5 ml of K-10 agar was added. The composition of K-10 agar is:

| Beef extract | 1.5 g |
|---|---|
| Yeast extract | 3.0 g |
| Peptone | 6.0 g |
| Dextrose | 1.0 g |
| Agar | 15.0 g |
| Distilled water | q.s. to 1 liter |

The final drug concentration in the agar ranged from 100 $\mu$g/ml to 0.05 $\mu$g/ml. Organism growth control plates containing agar only were prepared and inoculated before and after the test plates. The organisms were applied to the agar surface of each plate with a Denly Multipoint Inoculator (which delivers approximately 0.001 ml of each inoculum) resulting in a final inoculum of $10^4$ CFU on the agar surface.

The plates were incubated at 37° C. for 18 hours and the MICs determined. The MIC is the lowest concentration of compound inhibiting growth of the organism.

The results of the agar dilution assays are as follows:

| Organism | MIC (µg/ml) |
|---|---|
| *Staphylococcus aureus* *SC1276 | 0.8 |
| *Staphylococcus aureus* SC2399 | 3.1 |
| *Staphylococcus aureus* SC2400 | 3.1 |
| *Streptococcus faecalis* SC9011 | 0.8 |
| *Streptococcus agalactiae* SC9287 | 0.8 |
| *Micrococcus luteus* SC2495 | <0.05 |
| *Escherichia coli* SC8294 | >100 |
| *Escherichia coli* SC10896 | >100 |
| *Escherichia coli* SC10909 | >100 |
| *Klebsiella aerogenes* SC10440 | >100 |
| *Klebsiella pneumonia* SC9527 | >100 |
| *Proteus mirabilis* SC3855 | >100 |
| *Salmonella typhosa* SC1195 | >100 |
| *Shigella sonnei* SC8449 | >100 |
| *Enterobacter cloacae* SC8236 | >100 |
| *Pseudomonas aeruginosa* SC8329 | >100 |

*SC denotes organisms from the culture collection of E. R. Squibb & Sons, Inc.

The susceptibility of a number of anaerobic bacteria was also determined by an agar dilution technique. Test organisms were prepared from 24–48 hour cultures grown in Chopped Meat Broth (Scott Laboratories, Fiskeville, R.I.) or from washings from chocolate agar slants. These slants were prepared by adding hemoglobin to Proteose #3 Agar (Difco) to a concentration of 1%. The growth was washed off the slants with Brain Heart Infusion Broth (BBL Microbiology Systems) and diluted to a density of $10^8$ CFU per ml. The subject compound was dissolved in the appropriate diluent at a concentration of 1000 µg/ml. Two fold dilutions were made in Yeast Beef Broth (Difco) resulting in a range from 1000 µg/ml to 0.5 µg/ml. A 1.5 ml sample from each dilution was placed into individual petri dishes to which 13.5 ml of DST agar (Oxoid USA, Inc., Red Branch Road, Columbia, Md.) containing 5% lysed sheep blood and 0.5 µg/ml vitamin K was added. The final drug concentration in the agar ranged from 100 µg/ml to 0.05 µg/ml. Organism growth control plates containing agar only were prepared and inoculated before and after the test plates. The organisms were applied to the surface of each plate with the Denly Multipoint Inoculator, which delivers approximately 0.001 ml of each organism, resulting in a final inoculum level of $10^5$ CFU on the agar surface. Plates were incubated at 37° C. for 18 hours in an anaerobe chamber (Forma Scientific, Marietta, Ohio) and the MIC values then determined. The MIC is the lowest concentration of antibiotic inhibiting growth of the organism.

The results of the agar dilution assays are as follows:

| Organism | MIC (µg/ml) |
|---|---|
| *Bacteroides thetaiotamicron* *SC9005 | 0.8 |
| *Bacteroides thetaiotamicron* SC10278 | >100 |
| *Bacteroides fragilis* SC9844 | >100 |
| *Bacteroides fragilis* SC10277 | 1.6 |
| *Bacteroides fragilis* SC11085 | 1.6 |
| *Clostridium histolyticum* SC8572 | <0.05 |
| *Clostridium perfringens* SC11256 | <0.05 |
| *Clostridium septicum* SC1780 | <0.05 |
| *Clostridium difficile* SC11251 | 50 |
| *Hemophilus vaginalis* SC8568 | <0.05 |
| *Hemophilus vaginalis* SC9640 | <0.05 |
| *Fusobacterium necrophorum* SC10338 | <0.05 |
| *Pseudomonas anaerobius* SC11263 | 0.1 |

*SC denotes organisms from the culture collection of E. R. Squibb & Sons, Inc.

EM5596 can be used as a growth promoter and to enhance the feed efficiency (amount of feed required to produce a unit of weight gain) in chickens and swine. Administration of EM5596 to chickens and swines can be accomplished conveniently by dissolving or suspending EM5596 in the drinking water of the animals or by adding EM5596 to the animals' feed. If EM5596 is added to the animals' feed, it will preferably be initially formulated as a feed supplement. EM5596 can be present in the feed of chickens at a concentration of 1 to 100 parts per million, preferably 10 to 20 parts mer million.

EM5596 can also be used as a disinfectant in hospitals, laboratories, or in any other area where the presence of gram positive bacteria is to be avoided.

Figure 2:
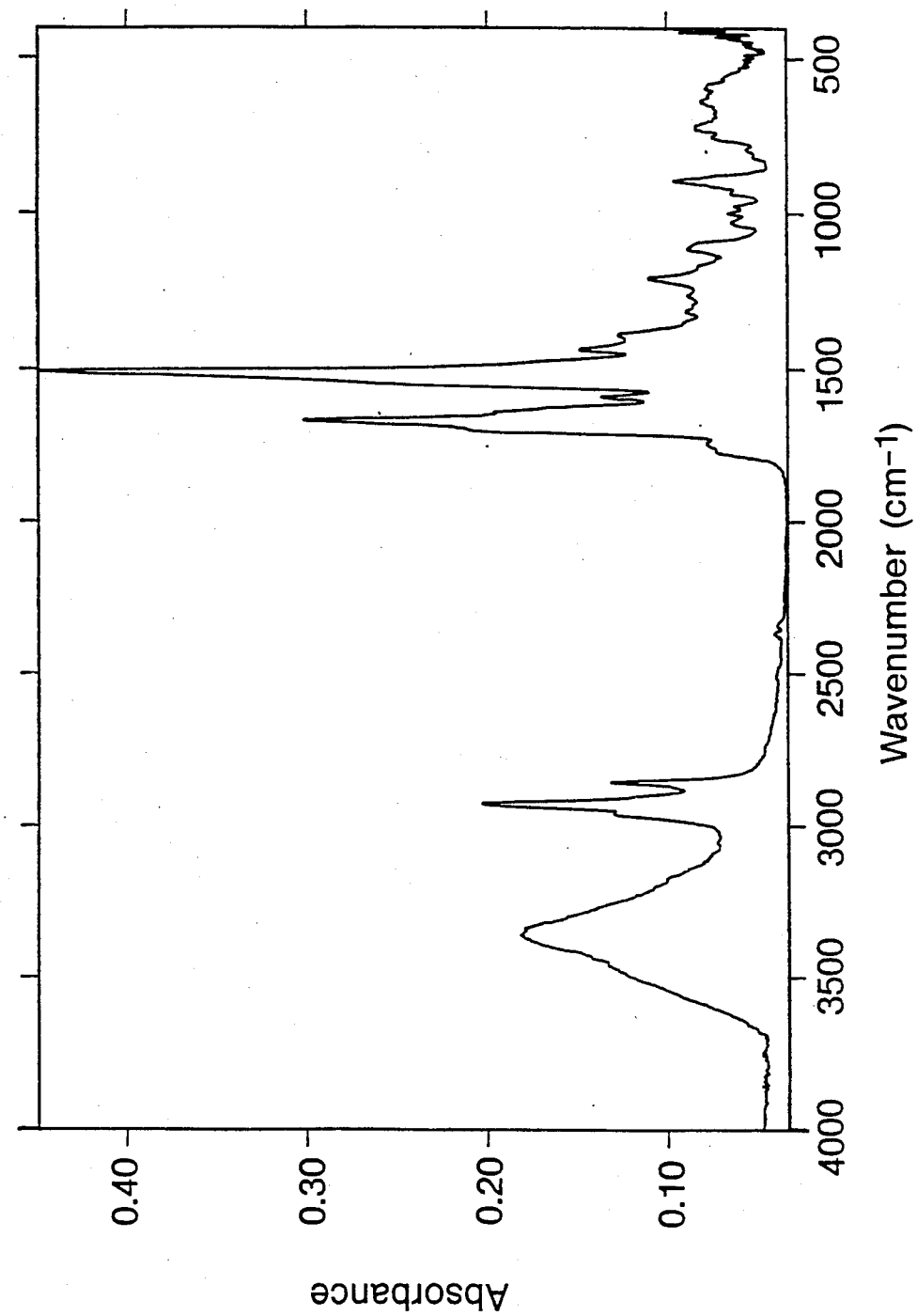
FIG. 2 shows the infrared spectrum of EM5596 in potassium bromide.
Figure 3:
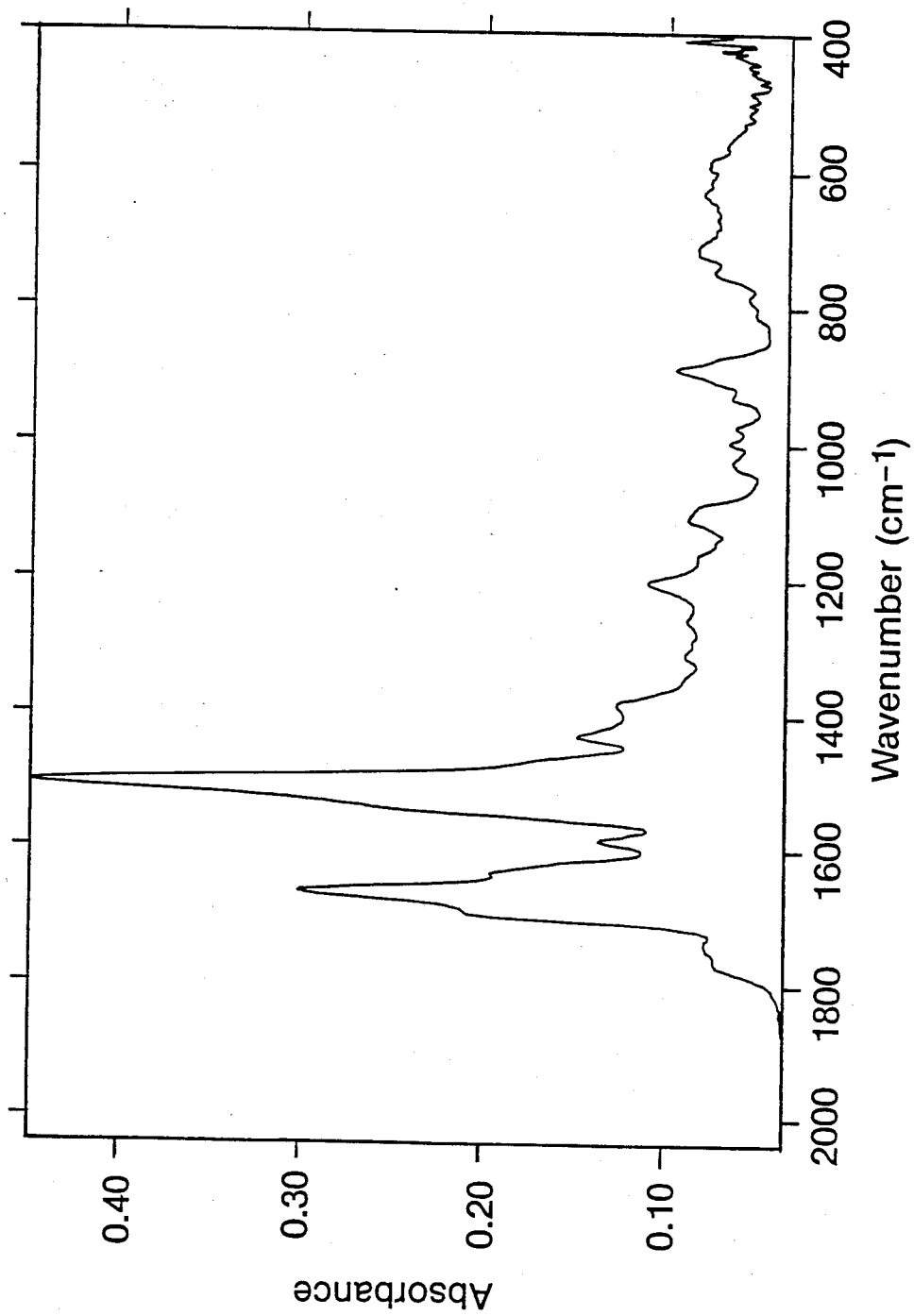
FIG. 3 shows a blow-up of that portion of the infrared spectrum of EM5596 in FIG. 2 having a wavenumber between 400 and 2000.
Figure 4:
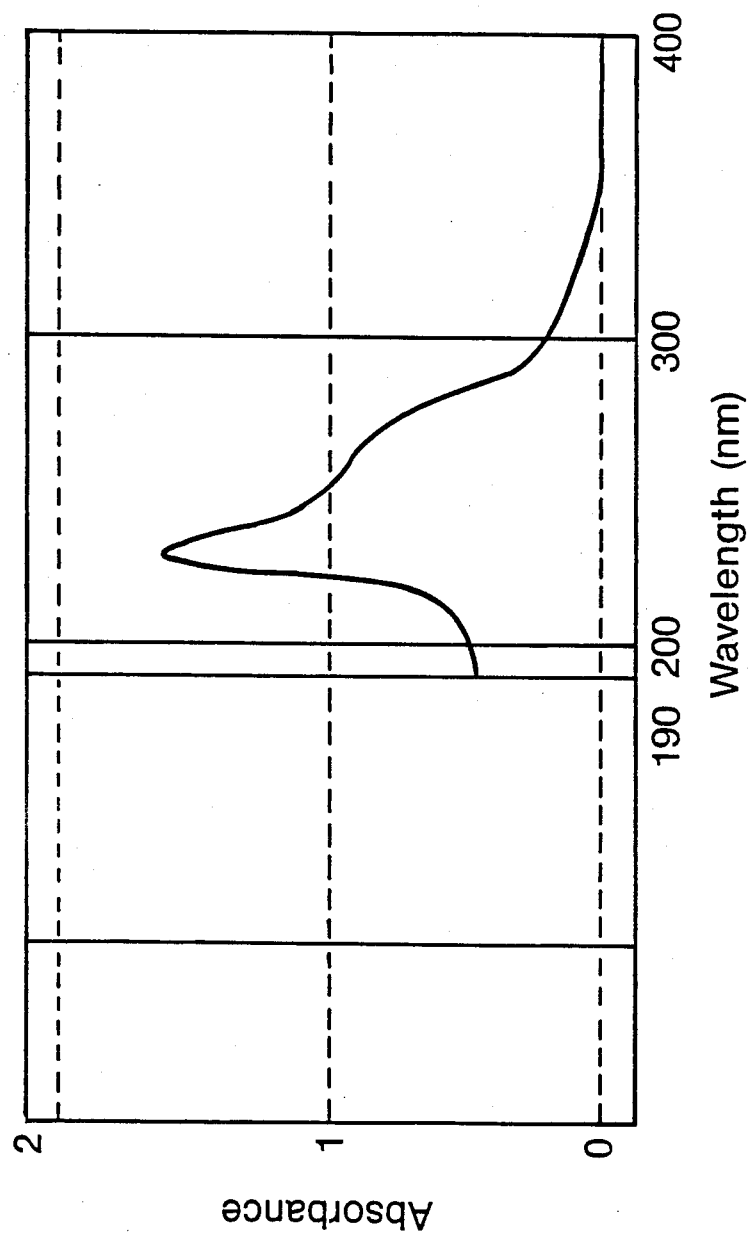
FIG. 4 shows the ultraviolet spectrum of EM5596 in acetonitrile.

What is claimed is:

1. EM5596, having the approximate elemental analysis C, 56.87; H, 6.56; N, 11.14; S, 3.3; having a 400 MHz $^1$H NMR spectrum in deuterated dimethylsulfoxide as in FIG. 1, having an infrared spectrum in potassium bromide as in FIGS. 2 and 3 and having an ultraviolet spectrum in acetonitrile as in FIG. 4.

2. A process for preparing EM5596 as defined in claim 1 which comprises cultivating *Micrococcus luteus* A.T.C.C. No. 53598 in a culture medium containing an assimilable source of carbon and an assimilable source of nitrogen until substantial antibiotic activity has been imparted to said medium, and then recovering EM5596 as defined in claim 1 from the medium.

3. A process in accordance with claim 2 where the organism is cultivated at about 25° C.

* * * * *